United States Patent
Nadolny et al.

(10) Patent No.: US 10,882,028 B2
(45) Date of Patent: Jan. 5, 2021

(54) NI-CONTAINING CATALYST FOR THE OLIGOMERIZATION OF OLEFINS

(71) Applicant: Evonik Operations GmbH, Essen (DE)

(72) Inventors: Fabian Nadolny, Arnsberg (DE); Stephan Peitz, Oer-Erkenschwick (DE); Guido Stochniol, Haltern am See (DE); Helene Reeker, Dortmund (DE); Wladimir Reschetilowski, Radebeul (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/293,717

(22) Filed: Mar. 6, 2019

(65) Prior Publication Data

US 2019/0283006 A1   Sep. 19, 2019

(30) Foreign Application Priority Data

Mar. 14, 2018   (EP) .................................... 18161747

(51) Int. Cl.
| | | |
|---|---|---|
| *B01J 23/78* | (2006.01) | |
| *B01J 21/12* | (2006.01) | |
| *B01J 35/02* | (2006.01) | |
| *B01J 35/10* | (2006.01) | |
| *B01J 37/00* | (2006.01) | |
| *B01J 37/02* | (2006.01) | |
| *B01J 37/04* | (2006.01) | |
| *B01J 37/08* | (2006.01) | |
| *C07C 2/12* | (2006.01) | |
| *B01J 23/755* | (2006.01) | |
| *C07C 2/10* | (2006.01) | |
| *B01J 35/00* | (2006.01) | |
| *B01J 23/02* | (2006.01) | |

(52) U.S. Cl.
CPC .............. *B01J 23/78* (2013.01); *B01J 21/12* (2013.01); *B01J 23/02* (2013.01); *B01J 23/755* (2013.01); *B01J 35/002* (2013.01); *B01J 35/023* (2013.01); *B01J 35/1019* (2013.01); *B01J 37/0009* (2013.01); *B01J 37/0018* (2013.01); *B01J 37/0063* (2013.01); *B01J 37/0201* (2013.01); *B01J 37/0236* (2013.01); *B01J 37/04* (2013.01); *B01J 37/08* (2013.01); *C07C 2/10* (2013.01); *C07C 2/12* (2013.01)

(58) Field of Classification Search
CPC ...... B01J 23/78; B01J 23/755; B01J 37/0009; B01J 35/002; B01J 23/02; B01J 21/12; B01J 35/023; B01J 35/1019; B01J 37/0018; B01J 37/0063; B01J 37/0201; B01J 37/0236; B01J 37/04; B01J 37/08; B01J 23/002; B01J 35/026; B01J 2523/00; C07C 2/10; C07C 2/12; C07C 2523/755; C07C 2521/12

See application file for complete search history.

(56) References Cited

U.S. PATENT DOCUMENTS

| | | | | |
|---|---|---|---|---|
| 2,581,228 A | * | 1/1952 | Bailey ..................... | C08F 10/00 502/259 |
| 3,557,242 A | * | 1/1971 | Sampson et al. ...... | B01J 23/755 585/516 |
| 3,658,935 A | | 4/1972 | Pine | |
| 5,849,972 A | | 12/1998 | Vicari et al. | |
| 7,939,597 B2 | | 5/2011 | Bub et al. | |
| 8,198,481 B2 | | 6/2012 | Kuppinger et al. | |
| 8,258,249 B2 | | 9/2012 | Bub et al. | |
| 8,293,941 B2 | | 10/2012 | Kuppinger et al. | |
| 8,481,784 B2 | | 7/2013 | Kuppinger et al. | |
| 8,524,945 B2 | | 9/2013 | Stochniol et al. | |
| 8,895,683 B2 | | 11/2014 | Kuppinger et al. | |
| 9,676,805 B2 | | 6/2017 | Dyballa et al. | |
| 9,845,276 B2 | | 12/2017 | Franke et al. | |
| 9,856,184 B2 | | 1/2018 | Stochniol et al. | |
| 10,155,200 B2 | | 12/2018 | Geilen et al. | |
| 10,189,755 B2 | | 1/2019 | Reeker et al. | |
| 10,196,327 B2 | | 2/2019 | Stochniol et al. | |
| 2004/0138059 A1 | * | 7/2004 | Euzen ..................... | B01J 35/10 502/255 |
| 2006/0070915 A1 | * | 4/2006 | Euzen ..................... | B01J 21/12 208/111.3 |
| 2006/0276334 A1 | | 12/2006 | Balduf et al. | |
| 2007/0118008 A1 | * | 5/2007 | Euzen ..................... | C10G 45/00 585/752 |
| 2009/0068440 A1 | | 3/2009 | Bub et al. | |

(Continued)

FOREIGN PATENT DOCUMENTS

| | | |
|---|---|---|
| DE | 10 2009 027408 A1 | 1/2011 |
| WO | 93/06926 A1 | 4/1993 |

(Continued)

OTHER PUBLICATIONS

Fridag et al., U.S. Appl. No. 16/203,929, filed Nov. 29, 2018.
Fridag et al., U.S. Appl. No. 16/204,263, filed Nov. 29, 2018.
Fridag et al., U.S. Appl. No. 16/204,572, filed Nov. 29, 2018.
Nadolny et al., U.S. Appl. No. 16/291,144, filed Mar. 4, 2019.
European Search Report dated Sep. 5, 2019 in EP 19162076.4 (3 pages).

(Continued)

*Primary Examiner* — Ali Z Fadhel
(74) *Attorney, Agent, or Firm* — Taylor English Duma LLP; Philip P. McCann

(57) ABSTRACT

The present invention relates to an oligomerization catalyst for oligomerization of low-molecular-weight olefins, to the use of said catalyst and to a process for oligomerization of low-molecular-weight olefins using the oligomerization catalyst according to the invention.

20 Claims, No Drawings

(56) References Cited

U.S. PATENT DOCUMENTS

| | | | |
|---|---|---|---|
| 2009/0192342 A1* | 7/2009 | Coupard | C07C 2/10 585/533 |
| 2012/0006724 A1* | 1/2012 | Du | B01J 37/036 208/110 |
| 2013/0172599 A1* | 7/2013 | Suzuki | B01J 21/08 560/208 |
| 2016/0145511 A1* | 5/2016 | Xu | C10G 69/02 208/60 |
| 2016/0257634 A1 | 9/2016 | Dyballa et al. | |
| 2017/0043323 A1* | 2/2017 | Du | B01J 35/002 |
| 2018/0072647 A1 | 3/2018 | Stochniol et al. | |
| 2018/0126361 A1 | 5/2018 | Klasovsky et al. | |

FOREIGN PATENT DOCUMENTS

| | | |
|---|---|---|
| WO | 95/14647 A1 | 6/1995 |
| WO | 2010/117539 A2 | 10/2010 |

OTHER PUBLICATIONS

Moussa et al., "Heterogeneous oligomerization of ethylene to liquids on bifunctional Ni-based catalysts: The influence of support properties on nickel speciation and catalytic performance," Catalysis Today, Copyright Jan. 2016, Elsevier, Amsterdam, NL, Bd. 277, pp. 78-88 (11 pages).
Nadolny et al., U.S. Appl. No. 16/293,702, filed Mar. 6, 2019.
Nadolny et al., U.S. Appl. No. 16/298,561, filed Mar. 11, 2019.
Nadolny et al., U.S. Appl. No. 16/293,859, filed Mar. 6, 2019.

\* cited by examiner

NI-CONTAINING CATALYST FOR THE OLIGOMERIZATION OF OLEFINS

CROSS REFERENCE TO RELATED APPLICATIONS

This application is a 35 U.S.C. § 119 patent application which claims the benefit of European Application No. 18161747.3 filed Mar. 14, 2018, which is incorporated herein by reference in its entirety.

FIELD

The invention relates to an oligomerization catalyst for oligomerization of low-molecular-weight olefins, to the use of said catalyst and to a process for oligomerization of low-molecular-weight olefins using the oligomerization catalyst according to the invention.

BACKGROUND

Oligomerization is generally understood as meaning the reaction of unsaturated hydrocarbons with themselves to form correspondingly longer-chain hydrocarbons, the so-called oligomers. Thus, for example, an olefin having six carbon atoms (hexene) can be formed by oligomerization of two olefins having three carbon atoms. The oligomerization of two molecules with one another is also referred to as dimerization.

The resulting oligomers are intermediates which may be used for example for the production of aldehydes, carboxylic acids and alcohols. The oligomerization of olefins is carried out on a large industrial scale either in the homogeneous phase using a dissolved catalyst or heterogeneously over a solid catalyst, or else with a biphasic catalyst system.

Among the heterogeneously catalysed processes, oligomerization over acidic oligomerization catalysts is long-established. Systems employed industrially include for example zeolites or phosphoric acid on a support. Isomeric mixtures of branched olefins are obtained here. For non-acidic, heterogeneously catalysed oligomerization of olefins with high dimer selectivity, nickel compounds on support materials are frequently employed in industry. Thus WO 95/14647 A1 describes a nickel catalyst comprising a support material consisting of the components titanium oxide and/or zirconium oxide, silicon oxide and optionally aluminium oxide for olefin oligomerization. Over these catalysts, mixtures of linear butenes are oligomerized to $C_8$-olefins with a selectivity of below 75%.

WO 95/14647 A1 describes a process for oligomerization of olefins by means of an oligomerization catalyst which as active constituents after subtracting the loss on ignition after heat treatment at 900° C. comprises 10% to 70% by weight of nickel oxide, calculated as NiO, 5% to 30% by weight of titanium dioxide and/or zirconium oxide, 0% to 20% by weight of aluminium oxide, 20% to 40% by weight of silicon dioxide and 0.01% to 1% by weight of an alkali metal oxide.

It is believed that the catalytic activity of nickel-based heterogeneous catalysts for the oligomerization of olefins, especially olefins having 2 to 8 carbon atoms, is based on the interaction between nickel cations and surface aluminium atoms. However, addition of titanium dioxide and zirconium dioxide has the result that the total composition contains a lower percentage of aluminium/aluminium oxide which results in the catalytic activity and/or the conversion, which can be achieved with the composition employed as catalyst, being reduced. At the same time, the addition of titanium dioxide and/or zirconium oxide may have the result that relatively large amounts of unwanted oligomerization products are formed, especially highly branched oligomers.

SUMMARY

The object of the present invention was to provide an improved oligomerization catalyst which can overcome the abovementioned disadvantages and which especially results in higher selectivities towards less branched products without any negative effect on the service life of the catalyst and the mechanical properties such as strength.

It has been found that, surprisingly, the inventive oligomerization catalyst according to claim 1 achieves the object of the invention. It has been found that, surprisingly, by dispensing with titanium dioxide and zirconium dioxide and by addition of comparatively small amounts of alkali metal or alkaline earth metal cations an oligomerization catalyst may be provided which in the oligomerization of olefins, in particular olefins having 3 to 6 carbon atoms, exhibits an enhanced selectivity for linear products without significantly reducing conversion. Small amounts of alkali metal cations in the context of the present invention is to be understood as meaning an at least tenfold excess of both nickel ions and optionally also aluminum ions compared to the molar proportion of alkali metal cations or alkaline earth metal cations.

DETAILED DESCRIPTION

The present invention accordingly provides in a first aspect an oligomerization catalyst which comprises nickel oxide, Al-containing and Si-free binder (<0.1 percent by weight of Si), a silica-alumina support material and an alkali metal or alkaline earth metal oxide, wherein the catalyst has a composition of 15% to 40% by weight, preferably 15% to 30% by weight, of NiO, 10% to 30% by weight, preferably 12% to 30% by weight, of $Al_2O_3$, 55% to 70% by weight of $SiO_2$ and 0.01% to 2.5% by weight, preferably 0.05% to 2% by weight, of an alkali metal or alkaline earth metal oxide, and wherein the oligomerization catalyst features a molar ratio of nickel ions:alkali metal/alkaline earth metal ions in the range from 1:0.1 to 1:0.001 and is substantially free from titanium dioxide and/or zirconium dioxide.

The alkali metal oxide or alkaline earth metal oxide is preferably an oxide of lithium, sodium, potassium, magnesium, calcium or a mixture thereof, more preferably of lithium, sodium, potassium or a mixture thereof, particularly preferably of lithium, sodium or a mixture thereof. In a particularly preferred embodiment the alkali metal or alkaline earth metal oxide is a lithium oxide.

The binder is a material which ensures that the catalyst produced in accordance with the invention has the necessary mechanical strength. In the context of the present invention "amorphous" is to be understood as meaning the property of a solid which results from the fact that it has no crystal structure, i.e. no long-range order. In the context of the present invention however it is not possible to preclude the amorphous silica-alumina support material having small crystalline domains. The amorphous silica-alumina support material is therefore not a crystalline material, for example not a zeolitic material.

In the context of the present invention the term substantially free from titanium dioxide and/or zirconium dioxide is to be understood as meaning that the oligomerization content has a content of titanium dioxide and/or zirconium dioxide of less than 0.5% by weight, preferably less than 0.1% by weight, particularly preferably less than 0.01% by weight.

According to the invention the oligomerization catalyst preferably also has a specific surface area (calculated according to BET) of 150 to 400 m$^2$/g, preferably 190 to 350 m$^2$/g, particularly preferably of 220 to 330 m$^2$/g. The specific surface area is measured and calculated by nitrogen physisorption according to DIN ISO 9277 (2014-01 version).

In a further preferred embodiment the oligomerization catalyst comprises mesopores and macropores, i.e. has a bimodal pore size distribution. The mesopores of the oligomerization catalyst according to the invention have an average pore diameter of 5 to 15 nm, preferably of 7 to 14 nm, particularly preferably of 9 to 13 nm. By contrast the macropores of the oligomerization catalyst according to the invention preferably have an average pore diameter of 1 to 100 µm, particularly preferably of 2 to 50 µm. The average pore volume of the oligomerization catalyst according to the invention, i.e. of both the mesopores and the macropores, may be 0.5 to 1.45 cm$^3$/g, preferably 0.7 to 1.13 cm$^3$/g. The average pore diameter and the average pore volume may be determined by mercury porosimetry according to DIN 66133 (1993-06 version).

The oligomerization catalyst according to the invention is preferably present in granulate form. Furthermore the oligomerization catalyst according to the invention may have an average particle diameter (d50) of 0.1 mm to 7 mm, preferably 0.5 to 6 mm, particularly preferably of 1 mm to 5 mm. The average particle diameter may be determined by imaging methods, in particular by the methods described in the standards ISO 13322-1 (2004-12-01 version) and ISO 13322-2 (2006-11-01 version). A suitable instrument for analysis of particle diameter is for example the Camsizer 2006 instrument (Retsch Technology).

In a further preferred embodiment the oligomerization catalyst has a bulk crush strength (BCS) of more than 0.5 MPa, preferably of more than 0.6 MPa and particularly preferably of more than 0.8 MPa. The BCS value is a measure of the mechanical strength of mineral granulates. The bulk crush strength (BCS) of a solid is to be understood as meaning a parameter defined as a pressure in MPa at which 0.5% by weight of fines fraction (i.e. particles screened off using a screen with a mesh size of 0.425 mm) are formed when the solid sample is subjected to pressure via a piston in a tube. For this purpose 20 ml of the solid are prescreened with a screen (mesh size: 0.425 mm), filled into a cylindrical sample tube (internal diameter: 27.6 mm, wall thickness: 5 mm, height: 50 mm) and 5 ml of steel spheres (diameter: 3.9 mm) are placed on the top surface of the solid. The solid is subsequently subjected to different (increasing) pressures for three minutes. The fines fractions formed by the subjection to pressure are then removed by screening, in each case weighed as a sum total and the percentage fraction thereof is determined. This process is performed until an amount of 0.5% by weight of fines fraction is reached.

An oligomerization catalyst may also be characterized by means of its maximum poured density. In a preferred embodiment the oligomerization catalyst according to the invention has a maximum poured density of 0.1 to 2 g/cm$^3$, preferably 0.2 to 1.5 g/cm$^3$, particularly preferably of 0.3 to 1.0 g/cm$^3$. Determination of poured density may be carried out via a measuring cylinder. The measuring cylinder is filled with a certain volume of the solid to be investigated, for example via a suitable metering apparatus such as the DR100 apparatus (Retsch) and the measuring cylinder is weighed. The maximum poured density may be determined from the weight and the volume. It may be necessary to subtract the residual moisture from the sample weight.

The oligomerization catalyst according to the invention is produced by a process comprising the steps of:

a) mixing the amorphous silica-alumina support material, the Al-containing and Si-free binder (<0.1% by weight of Si), at least a portion of the nickel source and optionally of the alkali or alkaline earth source; and granulating the thus-produced mixture;

a1) treating the granulate produced in step a) with at least a portion of a nickel source and/or an alkali or alkaline earth source provided that the entirety of the nickel source and/or the alkali metal or alkaline earth metal source has not already been mixed with the amorphous silica-alumina support material and the Al-containing and Si-free binder in step a), wherein the proportion of the amorphous silica-alumina support material in the total batch (total composition including any and all employed solvents) after step a) or a1) is 20% to 50% by weight, the proportion of the Al-containing and Si-free binder in the total batch is 5% to 30% by weight, the proportion of the alkali or alkaline earth source in undissolved form in the total batch is 0.01% to 2.5% by weight and the proportion of the nickel source in the total batch is 30% to 50% by weight; and b) drying and calcining the granulate to produce the oligomerization catalyst.

In a preferred embodiment all components (amorphous silica-alumina support material, Al-containing and Si-free binder, nickel source and alkali or alkaline earth source) are already mixed and granulated in step a). Step a1) is thus dispensed with.

The silica-alumina support material used in step a) is preferably an amorphous aluminosilicate. The amorphous silica-alumina support material is in particular not a zeolitic material. In a preferred embodiment the silica-alumina support material is an amorphous aluminosilicate comprising 10% to 20% by weight, preferably 12% to 17% by weight, of $Al_2O_3$ and 80% to 90% by weight, preferably 83% to 88% by weight, of $SiO_2$. The amorphous aluminosilicate employed as the silica-alumina support material may further preferably have a particle size (d50) in the range from 10 to 80 µm, preferably 15 to 75 µm, measured by laser diffraction, for example in a Malvern Mastersizer. The amorphous aluminosilicate employed as the silica-alumina support material moreover preferably has a specific surface area (calculated as BET) of 250 to 380 m$^2$/g, particularly preferably of 280 to 360 m$^2$/g, measured by nitrogen physisorption according to DIN-ISO 9277 (2014-01 version). The proportion of the silica-alumina support material in the total batch (total composition including any and all employed solvents such as water) in step a) is 20% to 50% by weight, preferably 25% to 45% by weight. If the entirety of the nickel source is not added to the total batch in step a) a sufficient amount of liquid to allow granulation should be added to the mixture in step a) by addition of a solvent, preferably water or an ammoniacal solution.

The Al-containing and Si-free binder likewise used in step a) (Si-free denotes: <0.1% by weight of Si in the total composition of the binder) is an oxidic aluminium material, preferably aluminium oxide, aluminium hydroxide or aluminium oxide hydroxide, particularly preferably boehmite. The Al-containing and Si-free binder is moreover preferably present not in solid form but rather in dissolved form, particularly preferably as a colloidal solution. In a preferred embodiment the solvent in which the Al-containing and Si-free binder, preferably aluminium oxide, aluminium hydroxide or aluminium oxide hydroxide, particularly preferably boehmite, is present in dissolved form, preferably as a colloidal solution, is a 1% by weight nitric acid solution. The Al-containing and Si-free binder is present in the colloidal solution, in an amount in the range from 10% to 25% by weight, preferably 12% to 20% by weight, particularly preferably 14% to 18% by weight. The proportion of the Al-containing and Si-free binder in the total batch (total composition including any and all employed solvents such as water) in step a) is 5% to 30% by weight, preferably 7% to 25% by weight.

An alkali metal or alkaline earth metal source, preferably an alkali metal or alkaline earth metal compound, is also added to the mixture in step a) or to the granulate in step a1). The alkali metal or alkaline earth metal compound may be in particular a lithium compound, sodium compound, potassium compound, magnesium compound, calcium compound or a mixture thereof, preferably a lithium compound, sodium compound, potassium compound or a mixture thereof, particularly preferably a lithium compound, a sodium compound or a mixture thereof. In a particularly preferred embodiment the alkali metal or alkaline earth metal compound is a lithium compound. Employable as the alkali metal or alkaline earth metal compound are in particular alkali metal or alkaline earth metal salts, preferably water-soluble alkali metal or alkaline earth metal salts, of the recited compounds.

Preferred alkali metal or alkaline earth metal salts are nitrates, carbonates or hydrogencarbonates of lithium, sodium, potassium, magnesium or calcium. Employable as the alkali metal or alkaline earth metal compound are in particular sodium carbonate, sodium hydrogencarbonate, potassium carbonate, potassium hydrogencarbonate, lithium carbonate or lithium hydrogencarbonate. In a particularly preferred embodiment the alkali or alkaline earth source, preferably the alkali metal or alkaline earth metal compound, is added as aqueous solution. In a further preferred embodiment, the alkali or alkaline earth source is added to the mixture in step a) and/or to the granulate in step a1) in a solution with the nickel compound. The proportion of the alkali or alkaline earth source (in undissolved form) in the total batch (total composition of any and all employed solvents such as water) in step a) or a1) of the production process is between 0.01% and 2.5% by weight, preferably 0.05% and 2% by weight.

The nickel source employed in step a) and/or a1) may in principle be any soluble nickel compound. Included among these are nickel nitrate ($Ni(NO_3)_2$), nickel acetate ($Ni(ac)_2$), nickel acetylacetonate ($Ni(acac)_2$), nickel sulfate ($NiSO_4$), nickel citrate or nickel carbonate ($NiCO_3$). Preference is given to nickel nitrate ($Ni(NO_3)_2$), nickel sulfate ($NiSO_4$), nickel carbonate ($NiCO_3$). Employable nickel sources include solutions of the abovementioned nickel compounds, pastes of the abovementioned nickel compounds or a combination of a nickel solution and a nickel paste.

The nickel solution is preferably an aqueous or ammoniacal solution. An ammoniacal solution is an aqueous solution admixed with ammonia. The nickel paste preferably contains water and the nickel paste according to the present invention contains less water than the nickel solution (when the same amount of nickel compound is assumed). If the alkali metal or alkaline earth metal source is added to the mixture in a solution with the nickel compound it is preferable to establish a molar ratio of nickel to alkali metal or alkaline earth metal cations of 1:0.001 to 1:0.1.

The nickel paste is in principle a moistened solid composed of a nickel compound which is incompletely hydrated and in which hydroxidic nickel compounds are formally also formed; in the case of nickel carbonate for example $NiCO_3*Ni(OH)_2$ but also non-stoichiometric nickel carbonate hydroxides. In a preferred embodiment the nickel paste contains between 30% and 50% by weight, preferably 35% to 45% by weight, of nickel based on the total weight of the paste. The nickel solution may contain nickel in an amount in the range from 1% to 20% by weight, preferably 5% to 15% by weight, in each case based on the total weight of the solution.

In a preferred embodiment the nickel solution employed is an aqueous, ammoniacal $Ni(CO_3)$ solution, known as NiHAC solution (a nickel hexamine carbonate complex is formed in the solution ($[Ni(NH_3)_6]CO_3$)) which has a nickel content in the range from 1% to 20% by weight, preferably 5% to 15% by weight. Employed as the nickel paste is a paste composed of nickel carbonate and water as solvent, wherein the nickel is present as carbonate/hydroxide (general empirical formula $NiCO_3*Ni(OH)_2$) but nonstoichiometric nickel carbonate hydroxides may also be formed). The paste may have a nickel content in the range from 30% to 50% by weight, preferably 35% to 45% by weight.

In a particularly preferred embodiment the production of the oligomerization catalyst employs in step a) and/or optionally a1) both a NiHAC solution and a nickel carbonate paste. This is to be understood as meaning that when the addition of the nickel source is carried out exclusively in the abovementioned step a) the nickel source may be added both in the form of a paste and in the form of a solution. This is also to be understood as meaning that when the addition of the nickel source is carried out partially in step a) and partially in step a1) the nickel source may be added in the form of a paste in one step a) or a1) and in the form of a solution in the other step a) or a1) or may be added both in the form of a paste and in the form of a solution in both steps a) or a1). In a particularly preferred embodiment for the mixture in step a) the at least one portion of the nickel source which is added to the mixture is a nickel paste.

The proportion of the nickel source (paste and/or solution) in the total batch (total composition of any and all employed solvents such as water) in step a) and optionally a1) of the production process is between 30% and 50% by weight, preferably 35% and 45% by weight.

The process according to the invention has the particular feature that in step a) or a1) no titanium dioxide and no zirconium dioxide are added to the mixture but rather the oligomerization catalyst is produced without addition of titanium dioxide and zirconium dioxide. Any incidences of titanium dioxide and/or zirconium dioxide in the total composition of the oligomerization catalyst are due to impurities/trace incidences in the employed components.

In step a) the individual components, i.e. the silica-alumina support material, the Al-containing and Si-free binder and optionally the nickel source, are mixed with one another in a mixing vessel using an agitator and simultaneously or subsequently granulated. This may be effected using an intensive mixer for example. Mixing and granulation may typically be performed at ambient pressure. The temperature at which mixing and granulation may be carried out is preferably in the range from 10° C. to 60° C. The duration of process step a), i.e. of mixing and granulation, is between 5 minutes and 1 hour, preferably between 10 and 30 minutes.

In optional step a1) the remaining portion of the nickel source, preferably in the form of a paste or a solution, is added to the granulate produced in step a) and mixed with the granulate in order to treat the granulate with nickel. If at least a portion of the nickel source is to be added in step a1) the possibly moist granulate from step a) may be dried prior to the treatment with the nickel source. The drying temperature may be 80° C. to 250° C., preferably 100° C. to 220° C.

The granulate resulting from step a) and/or step a1) may still contain at least a portion of the employed solvent, in particular water. A moist granulate may therefore be concerned. Before the possibly still moist granulate is subjected to the calcination in step b) the moist granulate may be screened, preferably with a screen having a mesh size of 0.1 to 1.5 mm. The screened-off portion of the granulate (undersize) may be recycled back to step a) of the granulation.

After the mixing and granulating in step a), optionally after the treating (impregnating) of a granulate with at least a portion of a nickel source in step a1) and optionally after the screening of the moist granulate the granulate may initially be dried in step b). This may be effected using known apparatuses such as for example belt dryers or the like. The drying temperature may be in the range from 80° C. to 250° C., preferably in the range from 100° C. to 220° C.

Before the optionally dried granulate is subjected to the calcination the dried granulate may be fractionated in order to establish a particular particle size of the granulate. Such a fractionation may be achieved for example through the use of at least one screen having a defined mesh size. In a particularly preferred embodiment two screens are used, wherein the one screen has a mesh size of 0.1 to 1.5 mm and the other screen has a mesh size of 2.5 to 7 mm. The remaining fractions (oversize and undersize) may be recycled to step a) optionally after preceding milling.

The optional drying and possible fractionation of the granulate is followed by the calcination of the granulate. This may comprise heating the granulate in a suitable furnace, preferably in a nitrogen stream, particularly preferably in a nitrogen countercurrent. Air may be added to the nitrogen stream during the calcination, wherein the amount of air supplied may be 100 to 10 000 ppm by volume, preferably 300 to 7000 ppm by volume. The calcination temperature may be 400° C. to 800° C., preferably 450° C. to 700° C., particularly preferably 500° C. to 600° C. This temperature may be maintained over several hours, preferably 5 to 20 hours, particularly preferably 8 to 15 hours, before the granulate is cooled. Air may be introduced into the furnace during cooling but the amount of air introduced should be controlled. The amount of the air optionally supplied is 100 to 10 000 ppm, preferably 300 to 7000 ppm.

The cooled granulate/the finished oligomerization catalyst may possibly then be fractionated once again to establish a particular particle size of the cooled granulate. Such a fractionation may be achieved for example through the use of at least one screen having a defined mesh size. In a particularly preferred embodiment two screens are used, wherein one screen has a mesh size of 0.1 to 1.5 mm and the other screen has a mesh size of 2.5 to 7 mm. The remaining fractions (oversize and undersize) may be recycled to step a) optionally after preceding milling.

After the last process step, of calcination and subsequent fractionation after cooling, the thus-produced oligomerization catalyst has a final total composition of 15% to 40% by weight, preferably 15% to 30% by weight, of NiO, 10% to 30% by weight, preferably 12% to 30% by weight, of $Al_2O_3$, 55% to 70% by weight of $SiO_2$ and 0.01% to 2.5% by weight, preferably 0.05% to 2% by weight, of an alkali metal or alkaline earth metal oxide. The figures are based on a total composition of 100% by weight.

A reduction in conversion and/or selectivity during oligomerization may be encountered with increasing employment time of the oligomerization catalyst. The catalyst according to the invention may be regenerated after use in the oligomerization reaction.

Regeneration of the oligomerization catalyst in the used state comprises the steps of:
  c) burnoff; and
  d) restoration of the active surface structure of the oligomerization catalyst.

After use in oligomerization reactions the oligomerization catalyst may exhibit deposits of organic substances that require removal. Removal of the organic compounds deposited in the catalyst is preferably accomplished in step c) by burnoff (oxidation) to form carbon oxides and water. The burnoff step c) may be performed continuously or discontinuously in a furnace, for example in a rotary kiln or a shaft furnace. For this purpose the oligomerization catalyst (in the form of a granulate) is supplied to the furnace and preferably maintained at a predetermined furnace temperature of 400° C. to 600° C., particularly preferably of 500° C. to 600° C. The combustion air used during burnoff is supplied in countercurrent and in addition further air is optionally blown into the granulate (oligomerization catalyst) via suitable inlets to ensure rapid burnoff.

Step d), i.e. the restoration of the active surface structure of the oligomerization catalyst may in a step d1) comprise an (additional) treatment (impregnation) with nickel. The treatment with nickel may be effected analogously to the production of the oligomerization catalyst (step a1)) but optionally with the difference that a nickel solution having a lower nickel concentration than in the production of the oligomerization catalyst may be used. A nickel paste is typically not employed in the regeneration. The aim here is to deposit additional amounts of nickel on the oligomerization catalyst. In principle any soluble nickel compound such as nickel nitrate ($Ni(NO_3)_2$), nickel acetate ($Ni(ac)_2$), nickel acetylacetonate ($Ni(acac)_2$), nickel sulfate ($NiSO_4$) or nickel carbonate ($NiCO_3$) may be used therefor to produce an aqueous or ammoniacal nickel solution.

The use of NiHAC solutions obtainable by dissolving nickel carbonate ($NiCO_3$) in concentrated ammonia solutions, optionally with addition of ammonium carbonate, has proven particularly advantageous. Such solutions may be used for the impregnation with nickel contents of 0.5 to 14% by weight, in particular of 2 to 10% by weight, very particularly of 4 to 8% by weight.

For nickel application the oligomerization catalyst burned off in step c) is for example impregnated with a NiHAC solution having nickel contents of 0.5 to 14% by weight, in particular of 2% to 10% by weight, very particularly of 4% to 8% by weight until saturation of the pores. The impregnation may be performed with a process familiar to those skilled in the art such as for example by spraying until permanent appearance of a liquid film on the surface (incipient wetness). If the solution takeup is about 0.8 to 1.2 g of solution per g of oligomerization catalyst a deposition of about 0.5% to 6% by weight of additional nickel in the form of a basic carbonate can be achieved.

If the oligomerization catalyst is subjected to a step d1), i.e. treated with nickel, the oligomerization catalyst should be dried in a suitable drying apparatus, for example a belt dryer with an air stream or else a conical dryer, at temperatures between 100° C. and 250° C., preferably between 120° C. and 220° C., and at standard pressure or else under vacuum.

Step d) comprises at least the step d2), the calcination that would be performed after an optional step d1). The calcination of the oligomerization catalyst may be performed continuously or discontinuously in a suitable furnace, for example a shaft furnace or rotary kiln. In the case of a continuous calcination in step d2) it is furthermore preferable when a gas continues to be passed through the oligomerization catalyst (granulate) in countercurrent. The gas employed may be air, nitrogen or a mixture thereof. The gas stream may be 0.2 to 4 m$^3$ of gas per kg of granulate and hour and the inlet temperature of the gas may be from 400° C. to 800° C., preferably 450° C. to 700° C. In addition to this heat introduced via the gas, energy may be introduced by active heating of the walls of the furnace.

The calcination temperature in the furnace may be 400° C. to 800° C., preferably 450° C. to 700° C., particularly preferably 500° C. to 600° C. This temperature may be maintained over several hours, preferably 5 to 60 hours, particularly preferably 10 to 40 hours, before the granulate is cooled. Cooling is preferably carried out in a nitrogen stream. Nitrogen may additionally be added to the air and the amount of air should preferably be controlled. The amount of air preferably added to the nitrogen may be 100 to 10 000 ppm by volume, preferably 300 to 7000 ppm by volume.

The oligomerization catalyst according to the invention/a catalyst produced or regenerated by the process according to the invention may be used in particular for the oligomerization of C3- to C6-olefins, preferably C3- to C5-olefins, particularly preferably C4-olefins, or olefin-containing input mixtures based thereupon. The olefins or olefin-containing input mixtures are employed as a reactant stream.

The present invention therefore also provides a process for oligomerization of C3- to C6-olefins, wherein an olefin-containing input mixture containing the C3- to C6-olefins is passed over a catalyst in at least one reaction zone, wherein the oligomerization catalyst according to the invention is employed to catalyse the oligomerization reaction. According to the invention a reaction zone comprises at least one reactor and at least one distillation column in which the oligomers formed may be separated. The process according to the invention may also be operated with two or more reaction zones. The oligomerization preferably takes place in the liquid phase.

Olefins employed for the process according to the invention include C3- to C6-olefins, preferably C3- to C5-olefins, particularly preferably C4-olefins or olefin-containing input mixtures based thereupon which may also contain proportions of analogous alkanes. Suitable olefins are inter alia α-olefins, n-olefins and cycloalkenes. The n-olefins used as reactants are preferred. In a particularly preferred embodiment, the olefin is n-butene. According to the invention the term "olefin-containing input mixtures based thereupon" is to be understood as encompassing any type of mixtures containing the relevant C3- to C6-olefins to be oligomerized in an amount which makes it possible to perform the oligomerization. The olefin-containing input mixtures preferably contain virtually no further unsaturated compounds and polyunsaturated compounds such as dienes or acetylene derivatives. It is preferable to employ olefin-containing input mixtures containing less than 5% by weight, in particular less than 2% by weight, of branched olefins based on the olefin proportion. It is further preferable to employ olefin-containing input mixtures containing less than 2% by weight of branched olefins, in particular isoolefins, such as isobutene.

Propylene (C3) is produced on a large industrial scale by cracking of naphtha and is a commodity chemical which is readily available. C$_5$-olefins are present in light petroleum fractions from refineries or crackers. Industrial mixtures containing linear C$_4$-olefins include light petroleum fractions from refineries, C$_4$-fractions from FC crackers or steam crackers, mixtures from Fischer-Tropsch syntheses, mixtures from the dehydrogenation of butanes, and mixtures formed by metathesis or from other industrial processes. Mixtures suitable for the process according to the invention are obtainable for example from the C$_4$-fraction of a steam cracker. Butadiene is removed in the first step here. This is accomplished either by extraction or extractive distillation of the butadiene or by selective hydrogenation thereof. In both cases a virtually butadiene-free C$_4$-cut is obtained, namely raffinate 1. In the second step, isobutene is removed from the C$_4$-stream, for example by production of methyl tert-butyl ether (MTBE) by reaction with methanol. Other options include the reaction of the isobutene from the raffinate I with water to afford tert-butanol or the acid-catalysed oligomerization of isobutene to afford diisobutene. The now isobutene-free C$_4$-cut, raffinate II, contains, as desired, the linear butenes and possibly butanes. The 1-butene may optionally still be removed by distillation. Both fractions, the one comprising but-1-ene or the one comprising but-2-ene, may be used in the process according to the invention.

In a further preferred embodiment C$_4$-olefin-containing material streams are supplied to the process as an olefin-containing input mixture. Suitable olefin-containing input mixtures are inter alia raffinate I (butadiene-free C4-cut from the steam cracker) and raffinate II (butadiene-free and isobutene-free C4-cut from the steam cracker).

A further option for producing suitable olefin-containing input mixtures is that of subjecting raffinate I, raffinate II or a similarly constituted hydrocarbon mixture to hydroisomerization in a reactive column. This may include inter alia a mixture consisting of 2-butenes, small proportions of 1-butene and possibly n-butane and also isobutane and isobutene.

The oligomerization is generally carried out at a temperature in the range from 50° C. to 200° C., by preference 60° C. to 180° C., preferably in the range from 60° C. to 130° C., and at a pressure of 10 to 70 bar, preferably of 20 to 55 bar. If the oligomerization is to be carried out in the liquid phase the parameters pressure and temperature must to this end be chosen such that the reactant stream (the employed olefins or olefin-containing input mixtures) is in the liquid phase. The weight-based space velocities (reactant mass per unit catalyst mass per unit time; weight hourly space velocity (WHSV)) are in the range between 1 g of reactant per g of catalyst and per h (=1 h$^{-1}$) and 190 h$^{-1}$, preferably between 2 h$^{-1}$ and 35 h$^{-1}$, particularly preferably between 3 h$^{-1}$ and 25 h$^{-1}$.

In one embodiment, the degree of dimerization (also referred to as "percentage selectivity based on dimerization") after the oligomerization based on the converted reactant is at least 60%, more preferably at least 75%, particularly preferably at least 80%.

The linearity of an oligomerization product/of the dimers formed is described by the ISO index and represents a value for the average number of methyl branches in the dimer. Thus (for butene as the reactant) n-octenes contribute 0, methylheptenes contribute 1 and dimethylhexenes contribute 2 to the ISO index of a C8 fraction. The lower the ISO index, the more linear the construction of the molecules in the respective fraction. The ISO index is calculated according to the following general formula:

$$\frac{\text{(singly branched dimers (\% by weight)} + 2 \times \text{doubly branched dimers (\% by weight))}}{100}$$

Accordingly a dimer mixture having an ISO index of 1.0 has on average precisely 1 methyl branch per dimeric molecule.

The ISO index of the product from the oligomerization process according to the invention is preferably 0.8 to 1.2, particularly preferably 0.8 to 1.1.

The oligomers produced by the process according to the invention are utilized inter alia for producing aldehydes, alcohols and carboxylic acids. Thus for example the dimerisation of linear butenes affords a nonanal mixture by hydroformylation. This provides either the corresponding carboxylic acids by oxidation or a $C_9$-alcohol mixture by hydrogenation. The $C_9$-acid mixture may be used for producing lubricants or siccatives. The $C_9$-alcohol mixture is a precursor for the production of plasticizers, particularly dinonyl phthalates, or DINCH.

Even without further elaboration it is assumed that a person skilled in the art will be able to utilize the description above to the greatest possible extent. The preferred embodiments and examples are therefore to be interpreted merely as a descriptive disclosure which is by no means limiting in any way whatsoever.

The present invention is more particularly elucidated hereinbelow with reference to examples. Alternative embodiments of the present invention are obtainable analogously.

EXAMPLES

Preparation of Catalyst 1a (Addition of Sodium):

Placed into the mixing vessel of an intensive mixer are a binder (solution composed of boehmite and a 1% by weight nitric acid solution, aluminium content between 15% to 17% by weight), a nickel source (nickel paste, moistened nickel carbonate, nickel content between 40% to 42% by weight) and amorphous silica-alumina (77.2% by weight $SiO_2$, 12.2% by weight $Al_2O_3$, remainder:water, ammonia, traces of further oxides, average particle size of 22 μm, specific surface area of 320 $m_2/g$).

The silica-alumina, the binder and the solid nickel source are mixed in the intensive mixer. During the commixing additional liquid components comprising a NiHAC solution (nickel carbonate dissolved in concentrated ammoniacal solution, nickel content between 11% and 12.5%) and an alkali metal compound (sodium carbonate dissolved in distilled water, ratio of nickel:sodium approximately 1:0.07) are slowly added into the mixing vessel via a funnel.

Once all components have been added the mixture is stirred at a relatively low speed to ensure effective distribution. A subsequent increase in the speed of the stirrer brings about a slow densification and granulation of the composition. Stirring is stopped as soon as granulates having a suitable particle diameter (0.1 mm to 7 mm) are obtained. The thus obtained granulate is dried at about 120° C. and subsequently screened using two screens to remove from the granulate excessively small or excessively large particles.

Granulate is then calcined in a furnace. For the calcination the granulate is heated to a temperature between 500° C. to 600° C. and this temperature is maintained for about 10 to 12 hours. The furnace filled with granulate has nitrogen flowing through it and a ratio of volumes of granulate to volumes of nitrogen per hour (standard volumes) of at least 1:1000 is maintained. During the cooling of the granulate to room temperature about 1000 to 10,000 ppm by volume of air are metered into the nitrogen stream. The cooled granulate corresponds to the finished oligomerization catalyst.

Preparation of Catalyst 1b (Addition of Lithium):

Catalyst 1b was prepared as per the process described for catalyst 1a with the exception that no sodium carbonate but rather an amount of lithium carbonate approximately equimolar to the sodium carbonate used for catalyst 1a (lithium carbonate dissolved in distilled water, ratio of nickel:lithium approximately 1:0.07) was added.

Preparation of Catalyst 1c (Addition of Potassium):

Catalyst 1b was prepared as per the process described for catalyst 1a with the exception that no sodium carbonate but rather an amount of potassium carbonate approximately equimolar to the sodium carbonate used for catalyst 1a (potassium carbonate dissolved in distilled water, ratio of nickel:potassium approximately 1:0.07) was added.

Preparation of Catalyst 1d (No Addition of an Alkali Metal or Alkaline Earth Metal):

Catalyst 1b was prepared as per the process described for catalyst 1a with the exception that no sodium carbonate, i.e. no alkali metal or alkaline earth metal compound, was added.

Use of the Catalysts in the Oligomerization:

Experimental Series 1 (Comparison of Catalyst 1a and 1d):

In experimental series 1 in each case about 4.5 g of the catalyst were filled into a differential circuit reactor and an oligomerization using feed material 1 (see table 1) was performed at a reaction pressure of 30 bar and a reaction temperature of 100° C. For experimental series 1 a loading of 7.5 g/h of butenes per gram of catalyst was employed.

Experimental Series 2 (Catalysts 1a, 1b and 1c):

About 12 g of the catalyst were filled into a metal tube having an internal diameter of 6 mm.

Placed in front of and behind the catalyst were glass pearls having a diameter of 2 mm which serve as a pre-heating/cooling phase. The oligomerization was performed using two different feed streams 2 and 3 at 30 bar and a loading of 7.5 g/h of butene per gram of catalyst, wherein the reaction temperature was 100° C.

TABLE 1

| Composition of feed streams | | | |
|---|---|---|---|
| | Feed stream 1 | Feed stream 2 | Feed stream 3 |
| isobutane | 0.1% | 8.0% | 0.3% |
| n-butane | 47.5% | 15.3% | 78.9% |
| trans-2-butene | 15.5% | 27.9% | 13.2% |
| 1-butene | 28.5% | 32.7% | 1.2% |
| isobutene | 0.1% | 0.9% | 0.1% |
| cis-2-butene | 8.3% | 15.2% | 6.1% |

The conversions and selectivities achieved as a function of temperature for the respective feed streams in the experimental series 1 and 2 and the iso-indices resulting therefrom are reported in tables 2, 3 and 4.

TABLE 2

Results of oligomerization in experimental series 1

|  | Catalyst 1a (inventive) | Catalyst 1d (non-inventive) |
|---|---|---|
| Conversion of n-butene | 12.2% | 17.3% |
| 3,4-DMH* | 11.9% | 20.0% |
| 3-MH* | 58.6% | 58.9% |
| n-O* | 29.2% | 19.6% |
| ISO-index | 0.79 | 0.97 |

TABLE 3

Results of oligomerization in experimental series 2 with feed stream 2
Loading (Feed of C4 olefins in g/h per unit mass of catalyst in g) as WSHV: 7.5 h$^{-1}$

|  | Temperature | Conversion based on C4 olefins | ISO index |
|---|---|---|---|
| Catalyst 1a | 100° C. | 21.5 | 0.97 |
| Catalyst 1b | 100° C. | 29.9 | 0.97 |
| Catalyst 1c | 100° C. | 20.8 | 0.95 |

TABLE 4

Results of oligomerization in experimental series 2 with feed stream 3
Loading (Feed of C4 olefins in g/h per unit mass of catalyst in g) as WSHV: 7.5 h$^{-1}$

|  | Temperature | Conversion based on C4 olefins | ISO index |
|---|---|---|---|
| Catalyst 1a | 100° C. | 17.6 | 1.08 |
| Catalyst 1b | 100° C. | 21.1 | 1.08 |
| Catalyst 1c | 100° C. | 15.8 | 1.06 |

3,4-DMH=3,4-dimethylhexene
3-MH=3-methylheptene
n-O=n-octene

In summary, the present results in experimental series 1 show that while addition of an alkali metal compound such as sodium carbonate during production of the catalyst does reduce the conversion, the proportion of linear octene isomers is significantly increased. Since each molecule can only be converted once, the formation of the linear products is preferred over high conversion.

The results of experimental series 2 show that all tested alkali metal compounds show good conversions and high selectivities for linear oligomerization products (ISO index<1.1). In terms of the formation of n-octenes all catalysts provide comparable results so that, very generally, it may be assumed that the addition of various alkali metal compounds makes it possible to achieve an improvement compared to catalysts without additional alkali metal compound.

The invention claimed is:

1. An oligomerization catalyst comprising:
   an Al-containing binder comprising less than 0.1% by weight of Si in the total composition of the Al-containing binder,
   an amorphous silica-alumina support material,
   nickel oxide (NiO), and
   an alkali metal or alkaline earth metal oxide;
   wherein the oligomerization catalyst has a composition of:
   from 15% to 40% by weight of NiO,
   from 10% to 30% by weight of Al$_2$O$_3$,
   from 55% to 70% by weight of SiO$_2$, and
   from 0.01% to 2.5% by weight of the alkali metal or alkaline earth metal oxide,
   wherein the oligomerization catalyst has a molar ratio of nickel ions:alkali metal/alkaline earth metal ions in the range of from 1:0.1 to 1:0.001 and is substantially free from titanium dioxide and zirconium dioxide,
   wherein the oligomerization catalyst has a specific BET surface area of from 150 to 400 m$^2$/g, determined by nitrogen physisorption,
   wherein the oligomerization catalyst comprises mesopores and macropores, the mesopores having an average pore diameter of 5 to 15 nm, the macropores of the oligomerization catalyst having an average pore diameter of 1 to 100 μm, and
   wherein the average pore volume of the mesopores and the macropores is from 0.5 to 1.45 cm$^3$/g.

2. The oligomerization catalyst according to claim 1 having a molar ratio of nickel ions:aluminum ions:alkali metal/alkaline earth metal ions in the range of from 1:2:0.1 to 1:0.01:0.001, and wherein the mesopores have an average pore diameter of 7 to 14 nm, the macropores have an average pore diameter of 2 to 50 μm, and
   wherein the average pore volume of the mesopores and the macropores is from 0.7 to 1.13 cm$^3$/g.

3. The oligomerization catalyst according to claim 2, wherein the oligomerization catalyst has a specific BET surface area of from 190 to 350 m$^2$/g, determined by nitrogen physisorption.

4. The oligomerization catalyst according to claim 1, wherein the alkali metal oxide or alkaline earth metal oxide is an oxide of lithium, sodium, potassium, magnesium, calcium or a mixture thereof.

5. The oligomerization catalyst according to claim 1, wherein the oligomerization catalyst has a specific BET surface area of from 220 to 330 m$^2$/g, determined by nitrogen physisorption, and wherein the mesopores have an average pore diameter of 9 to 13 nm, the macropores have an average pore diameter of 2 to 50 μm, and
   wherein the average pore volume of the mesopores and the macropores is from 0.7 to 1.13 cm$^3$/g.

6. The oligomerization catalyst according to claim 1 wherein the catalyst comprises from 15% to 30% by weight of NiO, from 12% to 30% by weight of Al$_2$O$_3$, and from 0.05% to 2% by weight of the alkali metal or alkaline earth metal oxide.

7. A process for producing the oligomerization catalyst according to claim 1, comprising at least the steps of:
   a) mixing the amorphous silica-alumina support material, the Al-containing binder, at least a portion of a nickel oxide source and at least a portion of analkali or alkaline earth oxide source; and granulating the thus-produced mixture;
   a1) treating the granulate produced in step a) with at least another portion of a nickel oxide source and/or an alkali or alkaline earth oxide source,
   wherein the proportion of the amorphous silica-alumina support material in the total batch (total composition including any and all employed solvents) after step a) or a1) is from 20% to 50% by weight, the proportion of the Al-containing binder in the total batch is from 5% to 30% by weight, the proportion of the alkali or alkaline earth oxide source in undissolved form in the total batch is from 0.01% to 2.5% by weight and the proportion of the nickel oxide source in the total batch is from 30% to 50% by weight; and b) drying and calcining the granulate to produce the oligomerization catalyst.

8. The process according to claim 7, wherein the Al-containing binder employed in step a) is an oxidic aluminum material.

9. The process according to claim 7, wherein the amorphous silica-alumina support material employed is an amorphous aluminosilicate.

10. The process according to claim 7, wherein the calcination in step b) is performed at a temperature between 400° C. and 800° C.

11. The process according to claim 7, wherein the oligomerization catalyst has a final composition of from 15% to 40% by weight, of NiO, from 10% to 30% by weight of $Al_2O_3$, 55% to 70% by weight of $SiO_2$ and 0.01% to 2.5% by weight, of the alkali metal or alkaline earth metal oxide.

12. The process according to claim 7 wherein the oligomerization catalyst has a final composition of from 15% to 30% by weight of NiO, and from 0.05% to 2% by weight of the alkali metal or alkaline earth metal oxide.

13. The process according to claim 7, wherein the Al-containing binder employed in step a) is selected from the group consisting of aluminum oxide, aluminum hydroxide and aluminum oxide hydroxide.

14. The process according to claim 7, wherein the oligomerization catalyst has a final composition of from 15% to 30% by weight of NiO and 0.05% to 2% by weight of the alkali metal or alkaline earth metal oxide.

15. A process for oligomerization of C3- to C6-olefins comprising:
    contacting an olefin-containing feed mixture containing the C3- to C6-olefins with a catalyst comprising the oligomerization catalyst of claim 1 in a reaction zone.

16. The process for oligomerization according to claim 15, wherein C3- to C5-olefins are comprised in the olefin-containing feed mixture.

17. The process for oligomerization according to claim 15, wherein C4-olefins are comprised in the olefin-containing feed mixture.

18. The process for oligomerization according to claim 15, wherein the olefin-containing feed mixture contains less than 2% by weight of branched olefins.

19. The process for the oligomerization according to claim 15, wherein the contacting takes place in the liquid phase.

20. The process for the oligomerization according to claim 15, wherein the contacting is carried out at a pressure of from 10 to 70 bar and a temperature of from 50° C. to 200° C., with the proviso that if the contacting is carried out in the liquid phase the parameters pressure and temperature are chosen such that the the olefin-containing feed mixture is in the liquid phase.

* * * * *

UNITED STATES PATENT AND TRADEMARK OFFICE
CERTIFICATE OF CORRECTION

PATENT NO. : 10,882,028 B2
APPLICATION NO. : 16/293717
DATED : January 5, 2021
INVENTOR(S) : Fabian Nadolny et al.

Page 1 of 1

It is certified that error appears in the above-identified patent and that said Letters Patent is hereby corrected as shown below:

In the Claims

Column 14,
Line 52, "a portion of analkali or" should read -- a portion of an alkali or --.

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*